(12) United States Patent
Najafi et al.

(10) Patent No.: US 9,265,465 B2
(45) Date of Patent: Feb. 23, 2016

(54) PROBES HAVING DEPLOYABLE SITES AND METHODS FOR MAKING THE SAME

(75) Inventors: Khalil Najafi, Ann Arbor, MI (US); Daniel Egert, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 747 days.

(21) Appl. No.: 13/487,234

(22) Filed: Jun. 3, 2012

(65) Prior Publication Data

US 2012/0310067 A1 Dec. 6, 2012

Related U.S. Application Data

(60) Provisional application No. 61/493,432, filed on Jun. 4, 2011.

(51) Int. Cl.
| | |
|---|---|
| *A61B 5/04* | (2006.01) |
| *A61N 1/05* | (2006.01) |
| *A61B 5/00* | (2006.01) |
| *A61B 5/0478* | (2006.01) |

(52) U.S. Cl.
CPC .............. *A61B 5/685* (2013.01); *A61B 5/04001* (2013.01); *A61N 1/05* (2013.01); *A61B 2562/028* (2013.01); *A61N 1/0502* (2013.01); *A61N 1/0531* (2013.01); *A61N 1/0541* (2013.01); *A61N 1/0543* (2013.01)

(58) Field of Classification Search
CPC .. A61B 5/0478; A61B 5/0492; A61B 5/4058; A61B 5/4064; A61B 5/4076–5/4094; A61B 5/6846; A61B 5/6847; A61B 5/6848; A61B 5/685; A61B 5/6868; A61B 5/6882; A61B 2562/0209; A61B 2562/028; A61B 2562/043; A61B 2562/14; A61N 1/04; A61N 1/05; A61N 1/0502; A61N 1/0529; A61N 1/5032; A61N 1/0534; A61N 2001/36039; A61N 2001/37205

USPC ................................. 600/372, 377, 378, 393
See application file for complete search history.

(56) References Cited

U.S. PATENT DOCUMENTS

| | | | |
|---|---|---|---|
| 6,881,213 B2 * | 4/2005 | Ryan et al. ....................... 606/41 |
| 7,744,584 B2 | 6/2010 | Seward et al. |
| 7,798,385 B2 * | 9/2010 | Boyden et al. ............. 227/175.1 |
| 7,937,153 B2 | 5/2011 | Zhou et al. |
| 7,941,202 B2 | 5/2011 | Hetke et al. |
| 7,983,756 B2 | 7/2011 | Nicolelis et al. |
| 8,386,006 B2 * | 2/2013 | Schouenborg ................ 600/373 |
| 2003/0158566 A1 * | 8/2003 | Brett ................. A61B 17/3478 606/167 |
| 2005/0209564 A1 * | 9/2005 | Bonner et al. ................ 604/173 |

(Continued)

OTHER PUBLICATIONS

Daneshvar, E.D., et al., "Mechanical Characterization of Conducting Polymer Actuated Neural Probes under Physiological Settings," SPIE vol. 7642, 76421T, 2010 (pp. 1-10).

(Continued)

*Primary Examiner* — Lee S Cohen
*Assistant Examiner* — Erin M Cardinal
(74) *Attorney, Agent, or Firm* — Dierker & Associates, P.C.

(57) ABSTRACT

A probe for interfacing with biological tissue includes a shank. A site to receive a signal from or stimulate the biological tissue is deployably connected to the shank. An insulated interconnect is connected to the site to guide signals or a fluid between the site and the shank. An actuator displaces the site away from a protected position on the shank to a deployed position in the biological tissue to be monitored or stimulated by the site.

20 Claims, 9 Drawing Sheets

(56) References Cited

U.S. PATENT DOCUMENTS

| | | | |
|---|---|---|---|
| 2009/0177144 A1 | 7/2009 | Masmanidis et al. | |
| 2009/0299166 A1 | 12/2009 | Nishida et al. | |
| 2009/0299167 A1 | 12/2009 | Seymour | |
| 2010/0076536 A1* | 3/2010 | Merz et al. | 607/116 |
| 2011/0105872 A1* | 5/2011 | Chickering et al. | 600/365 |
| 2012/0083752 A1 | 4/2012 | Kipke et al. | |

OTHER PUBLICATIONS

Kozai, T.D., et al., "Insertion Shuttle with Carboxyl Terminated Self-assembled Monolayer Coatings for Implanting Flexible Polymer Neural Probes in the Brain," J. Neurosci Methods, 184(2), 2009, (pp. 199-205).

Lind, G., et al., "Gelatine-embedded Electrodes—a Novel Biocompatible Vehicle Allowing Implantation of Highly Flexible Microelectrodes," J. Neural Eng., vol 7, 2010 (pp. 1-10).

Pang, C., "Parylene Technology for Neutral Probes Applications," Thesis for California Institute of Technology, 2008 (191 pages).

Seymour, J.P., et al., "Neural Probe Design for Reduced Tissue Encapsulation in CNS," Science Direct, Biomaterials, vol. 28, 2007 (pp. 3594-3607).

Takeuchi, S., et al., "Parylene Felxible Neural Probe with Micro Fluidic Channel," IEEE, 2004 (pp. 208-211).

Zeng, F.G., et al., "Cochlear Implants: System Design, Integration, and Evaluation," IEEE Reviews in Biomedical Engineering, vol. 1, 2008 (pp. 115-142).

\* cited by examiner

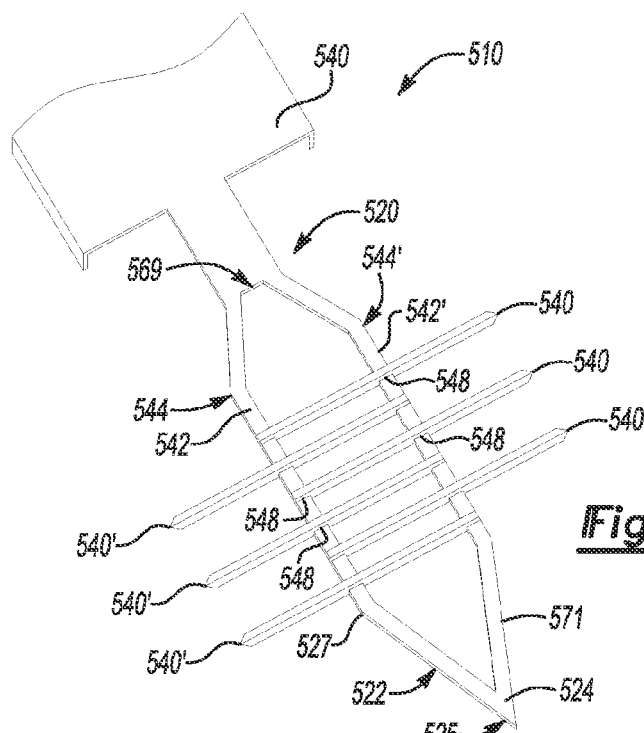
*Fig-8*
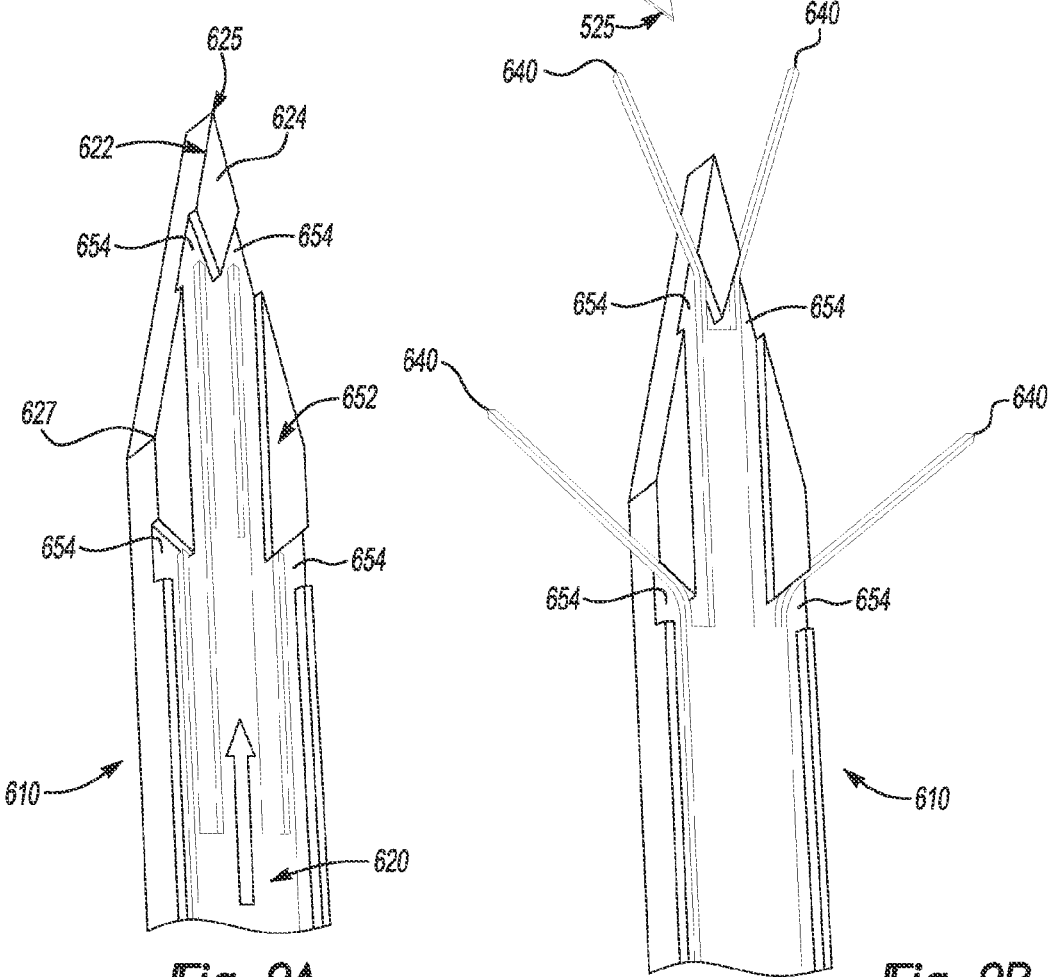
*Fig-9A*  *Fig-9B*

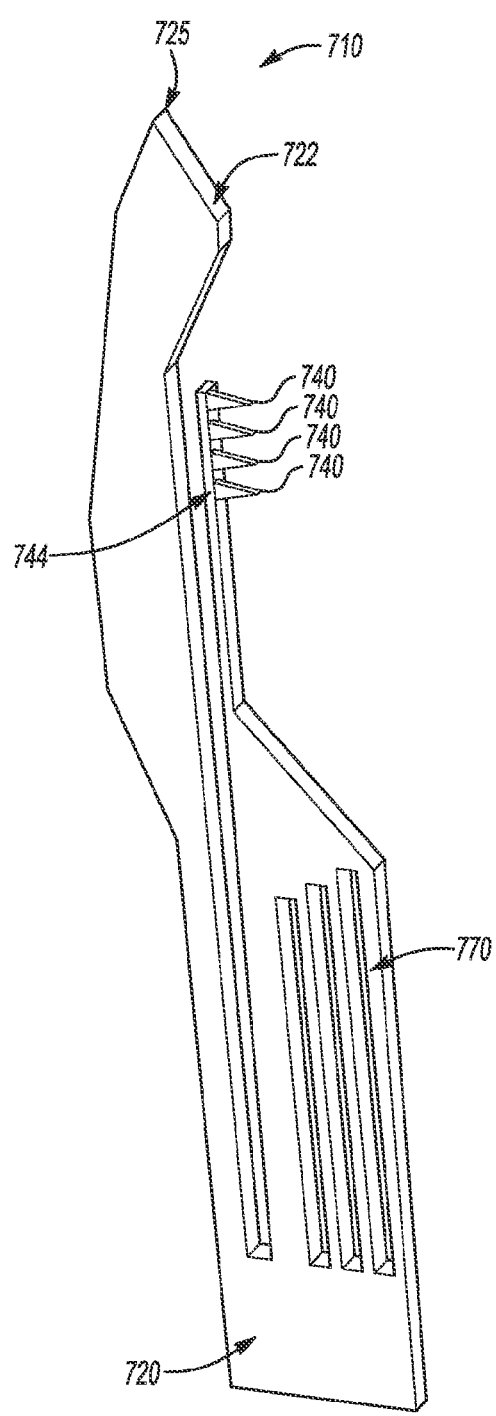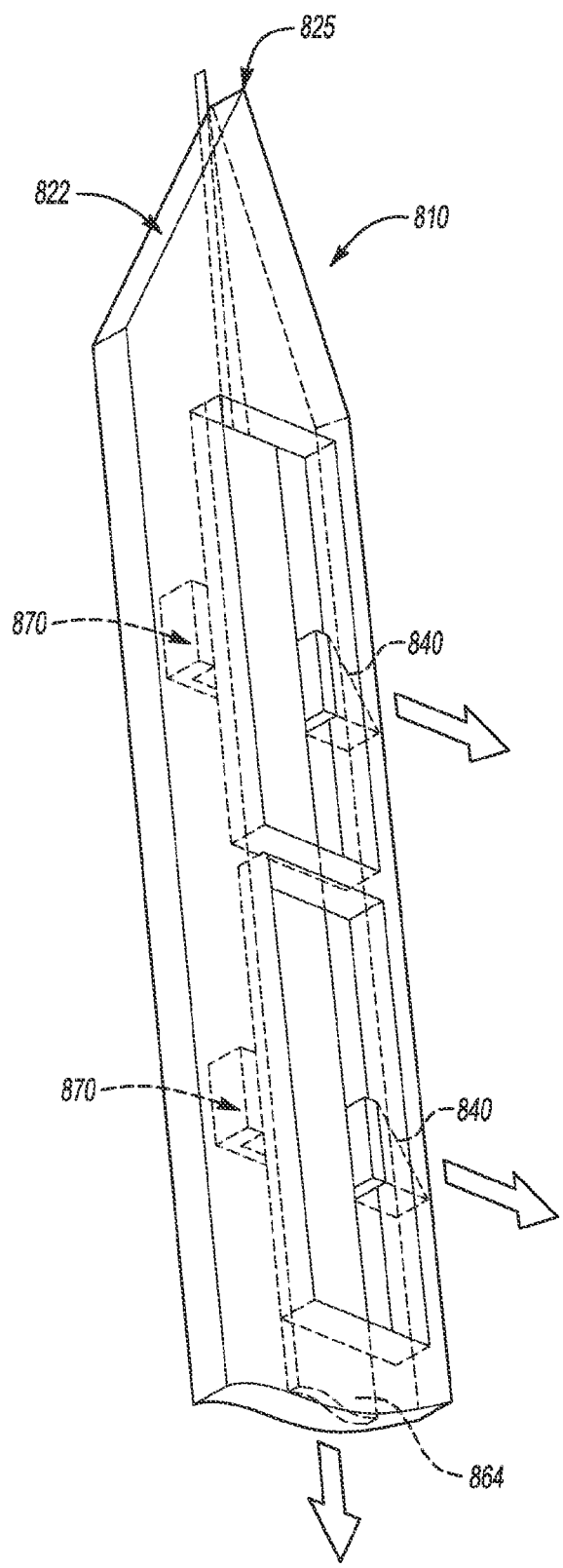
Fig-10
Fig-11

PROBES HAVING DEPLOYABLE SITES AND METHODS FOR MAKING THE SAME

CROSS-REFERENCE TO RELATED APPLICATIONS

This application claims the benefit of U.S. Patent Provisional Application Ser. No. 61/493,432, filed Jun. 4, 2011, which application is incorporated herein by reference in its entirety.

STATEMENT REGARDING FEDERALLY SPONSORED RESEARCH OR DEVELOPMENT

This invention was made with government support under N66001-07-1-2006 awarded by the U.S. Navy/SPAWAR. The government has certain rights in the invention.

BACKGROUND

The present disclosure relates generally to probes for electrical interfaces to biological tissue.

BRIEF DESCRIPTION OF THE DRAWINGS

Features and advantages of examples of the claimed subject matter will become apparent by reference to the following detailed description and drawings, in which like reference numerals correspond to similar, though perhaps not identical, components. For the sake of brevity, reference numerals or features having a previously described function may or may not be described in connection with other drawings in which they appear.

FIG. 8 is a semi-schematic view of an example of the probe disclosed herein with an actuator that retracts from implantation forces;

FIGS. 9A and 9B are semi-schematic views of an example of the probe disclosed herein;

FIG. 10 is a semi-schematic view of an example of the probe disclosed herein with a hot-cold actuator depicting the sites in the protected position;

FIG. 11 is a semi-schematic view of an example of the probe disclosed herein with a slide bar locking the actuators in the retracted position;

DETAILED DESCRIPTION

Figure 1:
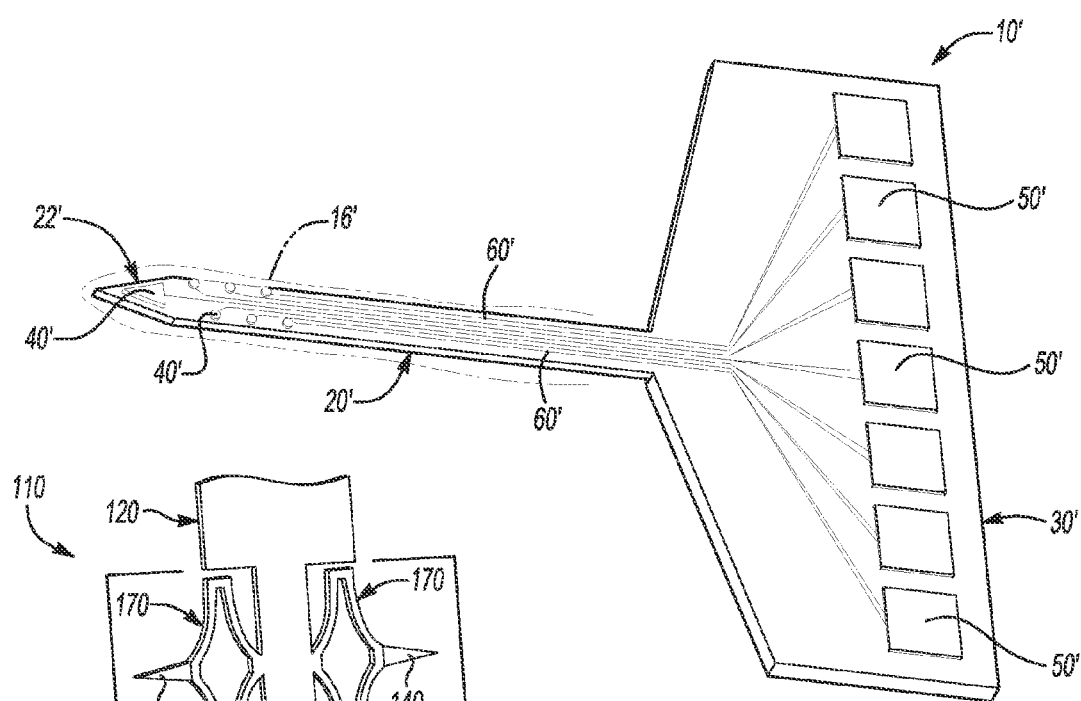
FIG. 1 is a semi-schematic perspective view of a prior art probe.

Probes having electrical interfaces to biological tissue have been used to read out biological signals, to artificially stimulate nerves or muscles, and to deliver drugs. Probes may include a needle-like shank hosting sites for recording or stimulation. The sites may be electrodes, openings of optical waveguides, chemical sensors, outlets- and inlets of fluid channels or structures for drug release. There are probes specialized to interface with various types of biological tissue such as: central nervous system (CNS) tissue—either penetrating into the tissue or resting on the surface as in an electrocorticogram (ECoG); peripheral nervous system tissues such as the cochlea or retina; and muscle tissue. The shanks for these implants are typically micro-fabricated and made of silicon, glass, diamond and polymers including Parylene, polyimide and silicone. Insulated interconnects guide signals or drugs along the shank between the sites and the backend. The backend may be used to establish a connection to other parts of an implant, for signal processing, data transmission or as a drug inlet. The sites may be in direct contact with the biological tissue of interest; however, non-contacting sites may sense or stimulate electrically over a short distance.

It is to be understood that some examples of the present disclosure may have no backend. In such examples, the shank may have functions similar to the backend described herein, without the probe including a backend portion. As used in examples of the present disclosure, "shank" means a substrate that supports an actuator. The actuator is connected to sites for recording or stimulation. In some examples of the present disclosure, the shank may be needle-shaped or blade-shaped. In other examples of the present disclosure, the shank may take any shape that allows the shank to support an actuator and allows the sites to be deployed. For example, the shank may be a flat disk, a flat rectangle, a round cylinder, a prism, etc.

In examples of the present disclosure, the backend or shank may also serve as an interface for components embedded in the probe. For example, the backend or shank may include connections for electrical leads that carry signals to and from electronic equipment that may include data collection equipment. The present disclosure also may include a wireless connection between the backend or shank and other systems. For example, electromagnetic signals (i.e. radio or optical signals) may be communicated through the backend or shank and remote systems. The remote systems may be outside of a biological host (e.g., a body of a human being, animal, insect, or plant), or may be within the biological host. For example, a probe may be located in one part of a body and communicate with a device in another part of the body.

Examples of probes disclosed herein may be autonomous and self-contained. For example, a probe may receive a signal and dispense a drug from a self-contained drug supply according to logic in an embedded microprocessor. Examples of the present disclosure may be powered through an external connection on the backend, or may be self-powered. It is to be understood that the connection may be wireless, for example an inductive connection may be used to provide power. Self-powered probes may include, for example, an electric battery, fuel cell, or generator. Self-powered probes may include a mechanical inertial power storage system similar to a self-winding wristwatch. Another example of a self-powered probe may include a piezoelectric device that harnesses a blood pressure pulse to generate electrical power.

FIG. 1 is a depiction of a prior art probe 10' used for interfacing with CNS tissue. FIG. 1 is included to provide context for the terminology used herein. The probe 10' includes a shank 20' and a backend 30' distal to the shank 20'. Seven sites 40' to receive a signal or stimulate biological tissue are depicted. Seven connectors 50' are shown corresponding to the seven sites 40'; each site 40' is connected to the respective connector 50' by insulated interconnects 60'. It is to be understood that all of the examples of the present disclosure may include a backend, connectors, and insulated interconnects similar to the backend 30', connector 50', and insulated interconnects 60' shown in FIG. 1. Because of the similarity and to avoid repetition, the backend, connectors, and insulated interconnects may not be shown in each figure. As stated above, some examples of the probe disclosed herein may not include a backend. When the probe 10' shown in FIG. 1 is inserted into biological tissue, a host response may diminish the chronic effectiveness of the sites 40' on the probe 10'. It has been shown that a dense sheath of scar tissue 16' may form within about 50 µm to about 150 µm of the implanted shank 20' of a probe 10' implanted in the central nervous system. The scar tissue 16' may displace neurons with cells that are part of an immune response. The monitoring/stimulation performance of sites 40' may be diminished as the distance to neurons exceeds a few tens of microns. Scar tissue 16' may significantly increase the impedance compared to cerebrospinal fluid. As such, the evoked host response may inhibit the stable exchange of information between the biological tissue and the sites 40' over time. It is to be understood that the leading edge 22' of the probe 10' shown in FIG. 1 may cause some cellular damage during insertion of the probe 10'. Shear stress between the probe 10' and the biological tissue from relative motion during insertion and chronic application may also cause cellular damage and elicit an immune system response.

It is to be understood that chronic means "long term" as used herein. For example, chronic use may be from about 1 day to 100 years. In chronic use, immune response may cause scar tissue to form.

Some examples of the present disclosure may be inserted into biological tissue where substantially no scar tissue forms. Deploying the sites away from the shank, for example, may move the sites into a different part of the biological tissue (i.e. a denser network of neurons) or penetrate a wall or sheath to access otherwise inaccessible biological material. In an example of the probes disclosed herein, deploying the sites may move the sites closer to active neurons for stimulation (i.e. in retinal implants or in cochlear implants).

Figure 2A:
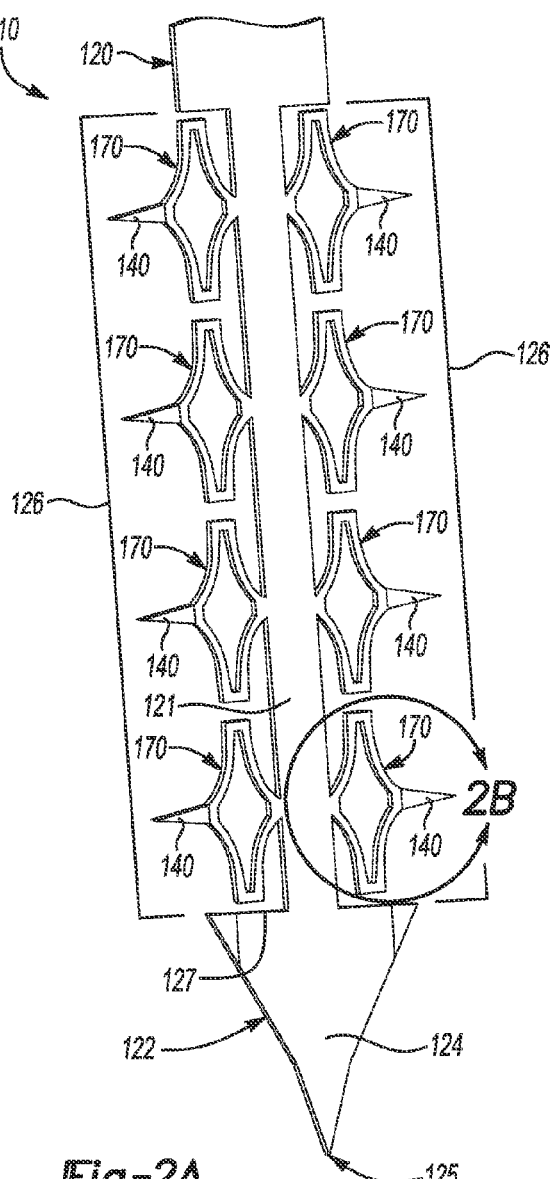
FIG. 2A is a semi-schematic view of a shank portion of a probe with deployed spring actuators in an example of the probe disclosed herein.

Referring now to FIG. 2A, an example of the probe 110 disclosed herein is depicted with the sites 140 deployed away from the needle-shaped or blade-shaped shank 120. The shank 120 includes a sharp point 124 at the tip 125 of the leading edge 122 of the shank 120. As depicted in FIG. 2A, the leading edge 122 may be wedge-shaped, having a trailing end 127 opposite the tip 125. The trailing end 127 may be larger than the point 124 in the dimension substantially perpendicular to the shank 120 and substantially in the plane of the shank 120. The leading edge 122 is configured to cut a path into the biological tissue and move the biological tissue aside during insertion of the probe 110 into the biological tissue. Recessed areas 126 defined along the shank 120 on opposite sides of the shank 120 are adjacent to the trailing end 127. The recessed areas 126 define a stem portion 121 of the shank 120 having a narrower cross section than the trailing end 127 of the leading edge 122. The recessed areas 126 define a protected area in which the sites are less subject to damage during implantation of the probe in biological tissue than areas outside of the protected area.

Figure 2B:
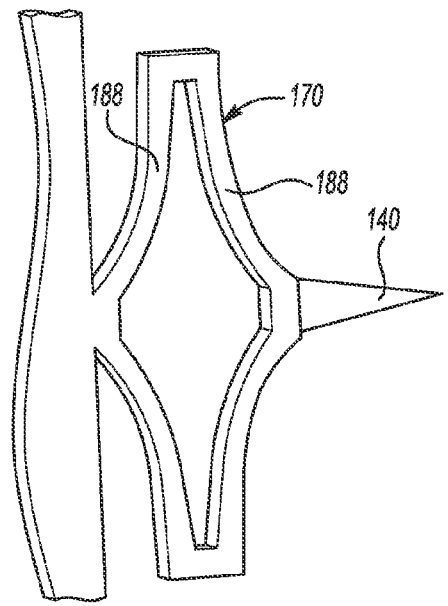
FIG. 2B is an enlarged view of the example of the spring actuator depicted in FIG. 2A.

As depicted in FIGS. 2A and 2B, spring actuators 170 are disposed along the stem portion 121. The spring actuators 170 have a deployed state shown in FIGS. 2A and 2B and a refracted state shown in FIG. 3A. A site 140 is disposed on each spring actuator 170 such that in the deployed state, the site 140 is embedded in the biological tissue to be monitored or stimulated. As such, in the deployed state, the sites 140 extend into the biological tissue beyond the path cut into the biological tissue during insertion of the probe 110 into the biological tissue.

Figure 3C:
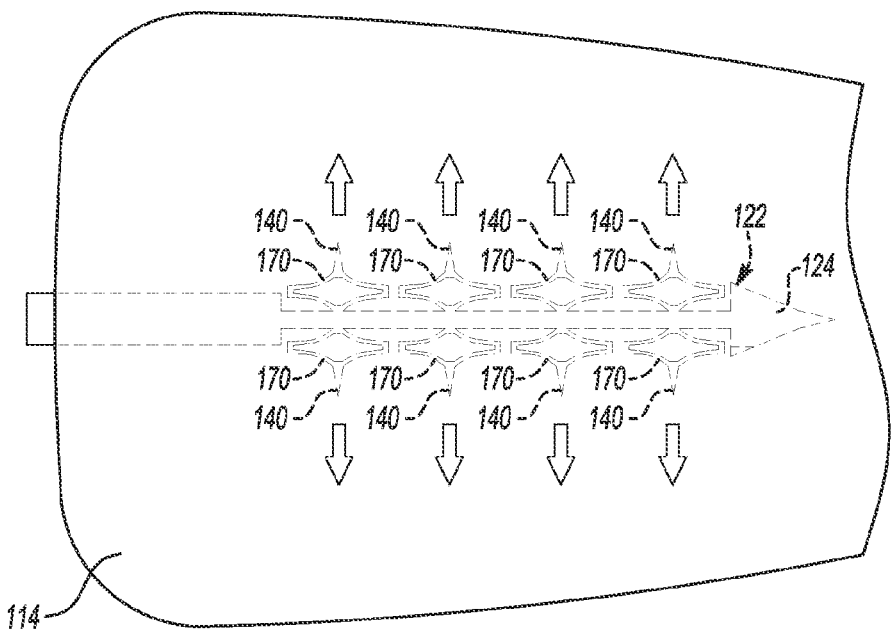
FIG. 3C is a semi-schematic view depicting the shank portion from FIG. 3A shown embedded in biological tissue with the spring actuators in the deployed position.

Still referring to FIGS. 2A and 2B, the spring actuator 170 in the free state may be in the form of opposed curved beams 188. When loaded transverse to the beams 188, the beams 188 deflect and straighten. When the beams 188 contact the adjacent beams 188 substantially along their entire length, the spring actuator 170 is at its solid height, and the actuator 170 is in the retracted state as shown in FIG. 3A.

The common elements of the probe 110 shown in subsequent Figures are numbered in the same sequence as the elements of the probe 110 shown in FIGS. 2A and 2B, except that the elements of the probe 110 are numbered in the 100, 200, 300 etc. series. That is, the common elements of the probe 110 may be identical to, or at least functionally similar to the elements of the other probes 210, 310, 410 etc. except as described below.

Figure 3B:
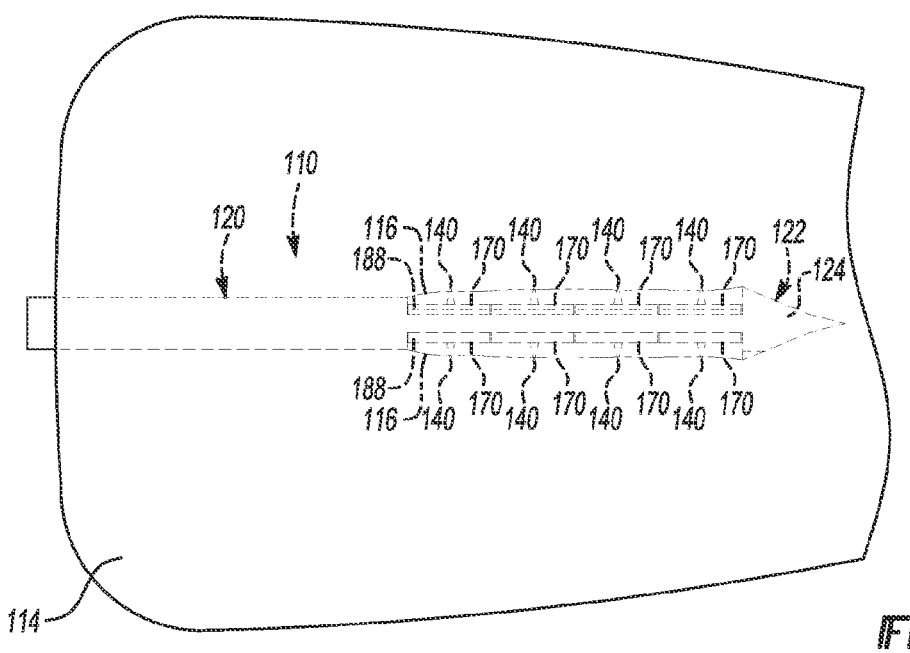
FIG. 3B is a semi-schematic view depicting the shank portion from FIG. 3A shown embedded in biological tissue with the spring actuators in the retracted position.
Figure 3A:
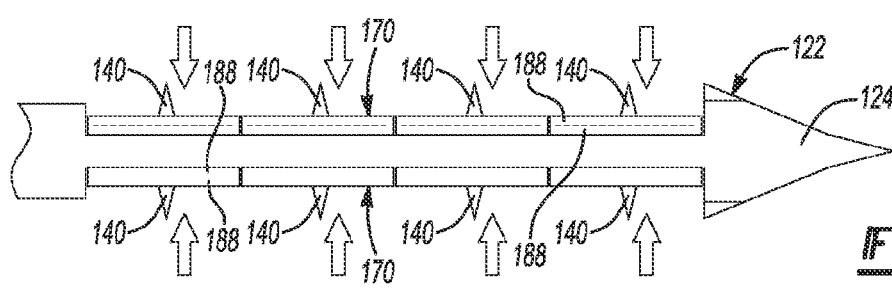
FIG. 3A is a semi-schematic view depicting the shank portion from FIG. 2A shown with the spring actuators in the retracted position.

FIG. 3B depicts an example of the disclosed probe 110 immediately after implantation in biological tissue 114. The spring actuators 170 are in the retracted state, and the sites 140 are shown in the protected positions. Scar tissue 116 is depicted in FIG. 3B, however it is to be understood that scar tissue 116 may not be immediately present upon implantation of the probe 110 in the biological tissue 114. As stated above, the scar tissue 116 may form within 50-150 µm of the implanted shank 120.

FIG. 3C depicts the example shown in 3B after the spring actuators 170 have deployed the sites 140 into the biological tissue 114. In examples where scar tissue forms around the probe 110 (see FIG. 3B), the spring actuators 170 may move to a deployed position spaced at least about 50 µm from the protected position (e.g. through the scar tissue 116). It is to be understood that the deployed position may be in a range from about 50 µm to about 500 µm from the protected position. In examples where scar tissue does not form, the spring actuators 170 may move to a deployed position spaced at least 1 μm to about 500 lam from the protected position.

It is to be understood that after the sites 140 have deployed into the biological tissue 114, the sites 140 may tend to float with the biological tissue 114 while remaining loosely connected to the probe 110. It is noted that the sites 140 are mechanically attached to the shank 120 through the spring actuators 170. The spring actuators 170 may be substantially more compliant/flexible than the shank 120 of the probe 110. The relative flexibility of the spring actuators 170 upon which the sites 140 may be disposed may float more freely with biological tissue 114 immediately proximate to the spring actuators 170. In contrast to the spring actuators 170, the shank 120 may be less able to move with the biological tissue 114 immediately surrounding the shank 120.

Figure 4C:
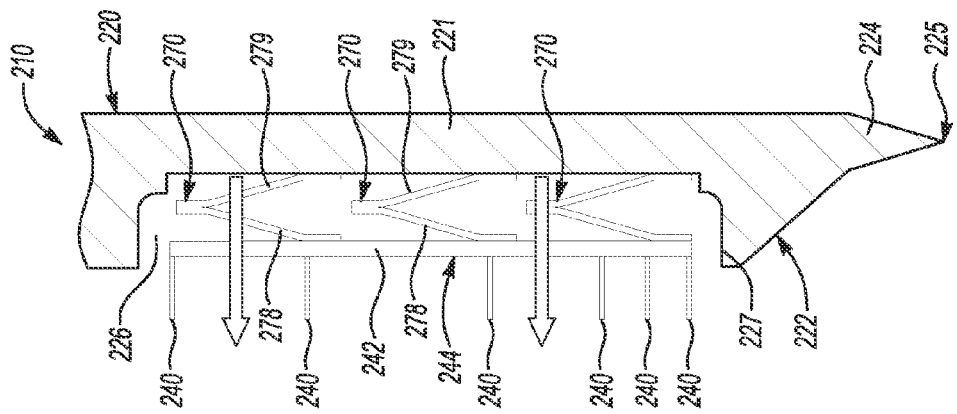
FIG. 4C is a semi-schematic view of the shank portion shown in FIG. 4A depicting the deployment of the sites away from the shank into biological tissue.
Figure 4B:
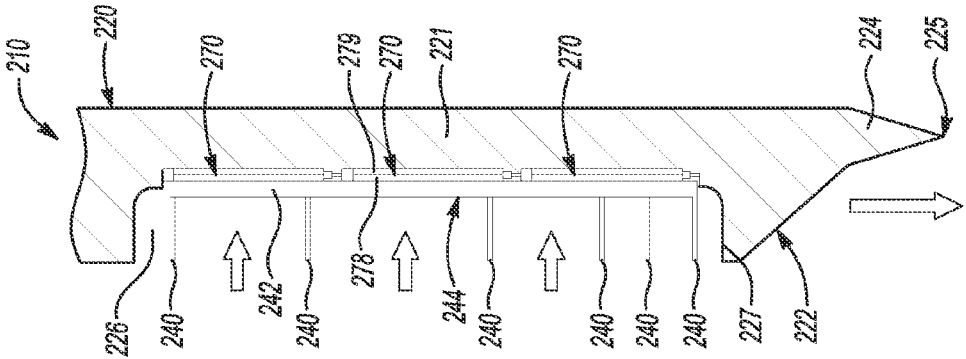
FIG. 4B is a semi-schematic view of the shank portion depicted in FIG. 4A with the spring actuators retracted in the protected position.
Figure 4A:
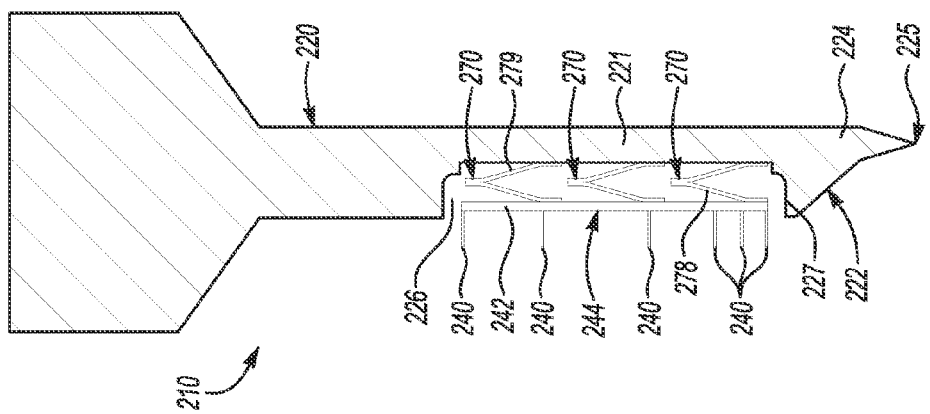
FIG. 4A is a semi-schematic view of a shank portion of another example of the probe with the spring actuators in the free state.

FIGS. 4A-4C depict another example of the probe 210. In FIG. 4A, the sites 240 are shown deployed away from the needle-shaped or blade-shaped shank 220. The shank 220 includes a sharp point 224 at the tip 225 of the leading edge 222 of the shank 220. As depicted in FIG. 4A, the leading edge 222 may be wedge-shaped, having a trailing end 227 opposite the tip 225. The trailing end 227 may be larger than the point 224 in the dimension substantially perpendicular to the shank 220 and substantially in the plane of the shank 220. The leading edge 222 is configured to cut a path into the biological tissue and move the biological tissue aside during insertion of the probe 210 into the biological tissue. Recessed area 226 is defined along the shank 220 on one side of the shank 220 and adjacent to the leading edge 222. The recessed area 226 defines a stem portion 221 of the shank 220 having a narrower cross section than the trailing end 227 of the leading edge 222. The recessed area 226 defines a protected area in which the sites 240 are less subject to damage during implantation of the probe 210 in biological tissue than areas outside of the protected area.

As depicted in FIGS. 4A-4C, spring actuators 270 are disposed along the stem portion 221. The spring actuators 270 have a deployed state shown in FIGS. 4A and 4C and a refracted state shown in FIG. 4B. A substantially rigid spine 242 spans the spring actuators 270 such that in the deployed state, the spine 242 substantially abuts the boundary between the protected area and the biological tissue. A plurality of sites 240 is shown extending from the spine 242 away from the stem portion 221 and into the biological tissue to be monitored or stimulated. The plurality of sites 240 and the spine 242 together may be referred to as a comb 244. As such, in the deployed state, the sites 240 extend into the biological tissue beyond the path cut into the biological tissue during insertion of the probe 210 into the biological tissue.

Still referring to FIGS. 4A and 4C, the spring actuator 270 in the free state may be a wishbone-shaped bow spring. The term wishbone-shaped as used herein means shaped like the furcula of a chicken or turkey. Each example of a spring actuator 270 depicted in FIGS. 4A-4C includes a spine portion 278 attached to the spine 242 and a shank portion 279 attached to the stem portion 221 of the shank 220. When in the retracted state shown in FIG. 4B, the spring actuators 270 have energy stored in them that causes the spring actuators 270 to move toward the deployed state unless the spring actuators 270 have a retracting force applied to them. The retracting force overcomes the spring force that biases the spring actuators 270 to the free state. Consequently, the retracting force moves the spring actuators 270 to the retracted state and selectively releasably retains the spring actuators 270 in the retracted state.

The retracting force may be externally applied by a mechanical means, for example by a micro-manipulator, or by applying the force with a contacting tool. Alternatively, the retracting force may be applied by direct impingement of a forced convection fluid stream. For example, an air jet may be directed at the comb in a direction to cause the actuator springs 270 to retract. In still further another example, the motion of a fluid stream may generate a pressure differential that causes a retracting force. Electric, magnetic, and thermal fields may further be used to apply a retracting force. Capillary action forces may also be used to retract the actuator springs 270. In examples disclosed herein, capillary forces may be manipulated using electrowetting to retract the actuator springs.

Figure 5A:
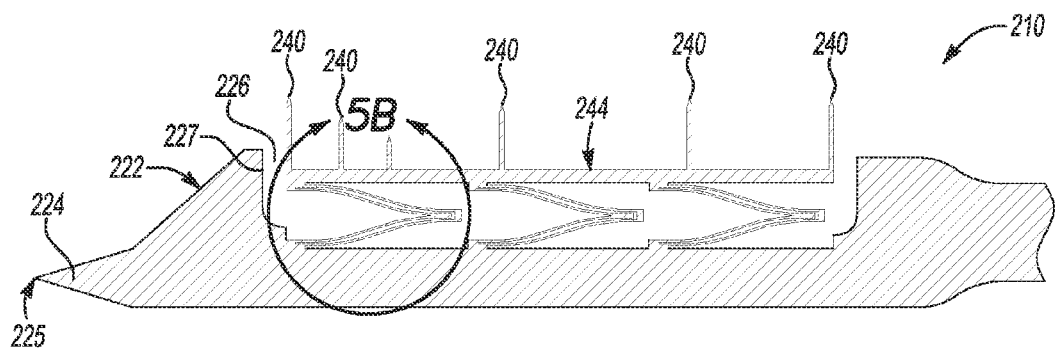
FIG. 5A is an enlarged view of a portion of the shank shown in FIG. 4A showing examples of dimensions.
Figure 5B:
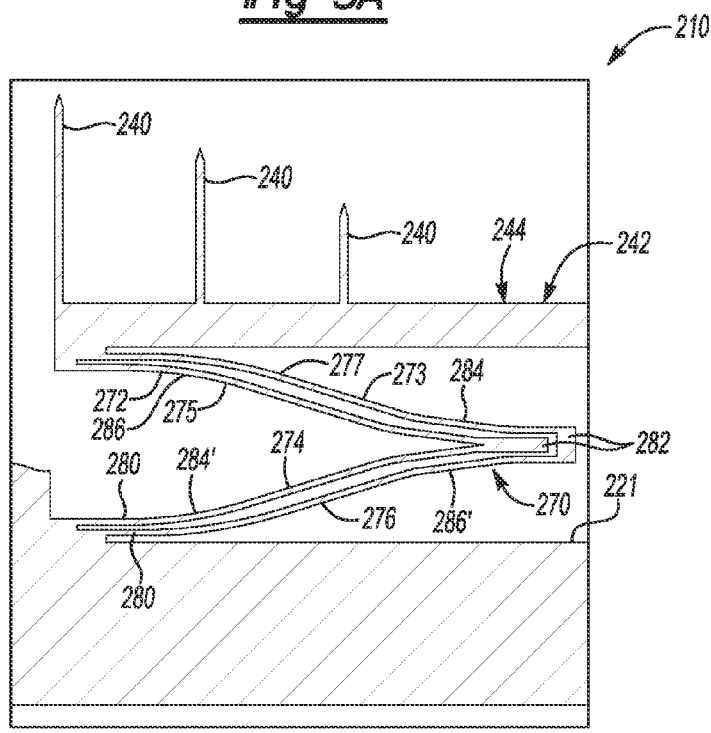
FIG. 5B is an enlarged view depicting an example of a nested double bow spring actuator.
Figure 5C:
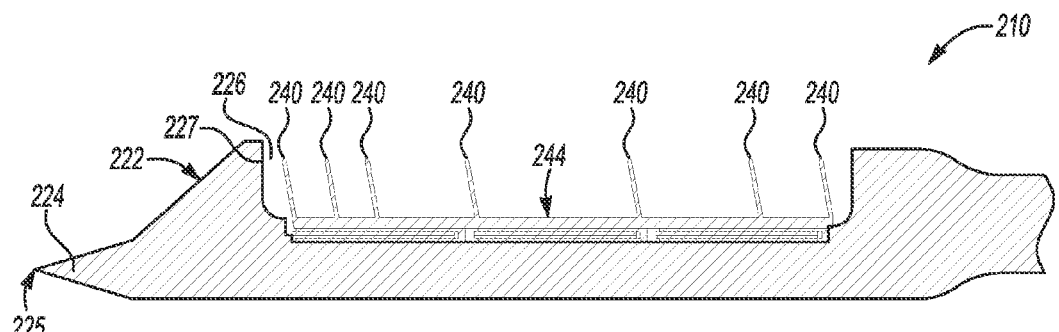
FIG. 5C is a semi-schematic view of the portion of the shank shown in FIG. 5A with the spring actuators shown in the retracted position, and the sites in the protected position.

For example, capillary action forces may be used to retract the actuator springs 270 depicted in FIGS. 5A-5C. Introduction of a wetting fluid causes forces related to capillary action to draw together adjacent surfaces of the actuator spring 270 as well as adjacent surfaces of the actuator spring 270 and the stem portion 221 and/or the spine 242. Without being bound to any theory, it is believed that capillary action's combination of surface tension from intermolecular cohesive forces and forces of adhesion between the liquid and the surface in contact with the liquid act upon the liquid and the surface. Such forces may cause the adjacent surfaces to be drawn together by the same type of attractive forces that cause a contact lens to adhere to a cornea. The wetting fluid must wet the surfaces to be joined in order to be effective as a retractive agent. It is to be understood that the surfaces may be treated to enhance wettability with the wetting fluid.

Sugar, agar gel, sugar saccharides, gelatin or combinations thereof, for example, may be added to water to act as glue, locking the sites 240 close to the shank 220. Capillary action from the water pulls the glue agents between and around the surfaces to be adhered. The glue holds the actuator springs 270 in the retracted position once the water is evaporated. The dissolvable glue may introduce a time delay after implantation before deployment of the sites 240 by the actuator springs 270. Additionally, the glue additives may enhance the surface tension of water, or form a gel around the actuator springs 270 that, when drying, shrinks and retracts the actuator springs 270.

FIG. 4B depicts an example of the disclosed probe 210 in the retracted state before implantation in biological tissue. The spring actuators 270 are in the retracted state, and the sites are shown in the protected positions. In examples of the disclosed probe 210, the spring actuators 270 may be retained in the retracted position until automatically released or triggered by a change in environment during implantation. A chemical reaction that changes an adhesive or that is initiated by a change in pH, humidity, temperature or magnetic field strength may trigger an automatic release from the retracted position. For example, an adhesive may change by completely dissolving to release the spring actuators 270. However, the adhesive may change sufficiently to release the spring actuators 270 without dissolving. The adhesive material may swell and release from the spring actuators 270 thereby allowing the spring actuators 270 to move. After implantation of the probe 110, the glue (e.g., sugar, agar gel, etc.) may be released from the spring. The change in the glue may be a dissolving, delamination or swelling. In an example, the glue may swell and directly push a spring to a deployed state. In another example, the glue may swell and activate a mechanical trigger that releases the spring actuator to move to a deployed state.

In another example, the temperature of the biological tissue may be used to trigger the spring actuators 270. In another example, a biological fluid present in the biological tissue may trigger the spring actuators 270. In a pH activated trigger, the pH may be naturally occurring in the biological tissue, or the pH may be manipulated by applying an electric signal. In examples of the disclosed probe 210, the spring actuators 270 may be releasably retained in the retracted position by a glue dissolvable in the biological tissue. Non-limiting examples of a glue dissolvable in biological tissue include sugar, agar gel, gelatin, or combinations thereof.

FIG. 4C depicts the example shown in 4B after the spring actuators 270 have deployed the sites 240 into the biological tissue. It is to be understood that after the sites 240 have deployed into the biological tissue, the sites 240 may tend to float with the biological tissue while remaining loosely connected to the probe 210. In examples of the disclosed probe 210, the sites 240 may be firmly attached to the shank 220 through the spring actuators 270. As such, after the spring actuators 270 deploy, the sites 240 may float or may be more rigidly attached to the shank 220 depending on the stiffness of the spring actuators 270.

Capillary action force retraction and subsequent release triggered after implantation was experimentally demonstrated in a laboratory with a probe 210 similar to the probe shown in FIGS. 5A-5C. In the experiment, the springs 270 were retracted in water with 6 percent sugar by mass. The sugar solidified as the water evaporated and retained the spring actuators 270 in the retracted position. After the probe 210 was implanted into an agar brain surrogate, the sugar dissolved and the spring actuators 270 deployed.

In another experiment, the probes 210 were dipped into 0.6 percent agar solution, heated to 60° C. and dried at room temperature. While the residual water evaporated, the spring actuators 270 retracted automatically close to the shank 220. The probes 210 were implanted into a cadaver lamb brain and subsequently explanted and examined. It is to be understood that agar gel does not dissolve readily after implantation but may be broken down by an active immune system or by enzymes and/or hydrolysis. The cadaver lamb brain experiment was conducted to test if the probe shank 220 offers sufficient protection to the sites 240. The sites 240 remained in the retracted position throughout the experiment. Upon examination after explantation, it was revealed that the sites 240 were not damaged.

FIGS. 5A-5C depict enlarged semi-schematic views of the example of the probe 210 shown in FIGS. 4A-4C. As can be best seen in FIG. 5B, the spring actuator 270 may include a plurality of nested wishbone-shaped bow springs. As depicted in FIG. 5B, the spring actuator 270 may include an inner spring 272 and an outer spring 273. The inner spring 272 and the outer spring 273 each include a respective upper branch 275, 277 and a respective lower branch 274, 276. Thus, the four branches of the spring actuator 270 shown in FIG. 5B are the lower inner branch 274, the upper inner branch 275, the lower outer branch 276, and the upper outer branch 277. Each of the branches 274-277 of the spring actuator 270 functions elastically as a curved cantilever beam. In the example of the disclosed probe 210 shown in FIG. 5B, each of the lower branches 274, 276 has a fixed end 280 attached to the stem portion 221 and a quasi-free end 282 attached to the quasi-free end 282 of the corresponding upper branch 275, 277. Using the orientation shown in FIG. 5B, the upper branches 275, 277 have a concave down curved portion 286 proximate the fixed end 280 and a concave up curved portion 284 proximate the quasi-free end 282. The lower branches 274, 276 mirror the curvature of the upper branches 275, 277. More specifically, the lower branches 274, 276 have a concave up curved portion 284' proximate the fixed end 280 and a concave down curved portion 286' proximate the quasi-free end 282. When loaded transverse to the branches 274-277, the branches elastically deflect and straighten. When the branches 274-277 contact the adjacent branches substantially along their entire length, the spring actuator 270 is at its solid height, and the actuator 270 is in the retracted state as shown in FIG. 5C.

Examples of the probe 210 depicted in FIGS. 5A-5C have been experimentally produced. In one example, the shank consisted of silicon and had a uniform thickness of about 15 μm. The width of the comb 244 was about 130 μm. It is to be understood that this value was not optimized. The sites were arbitrarily spaced along the 1.1 mm long comb 244. As such, the sites 240 may be distributed arbitrarily within the protected area. The shank 220 had six spring actuators 270 in parallel.

Figure 13:
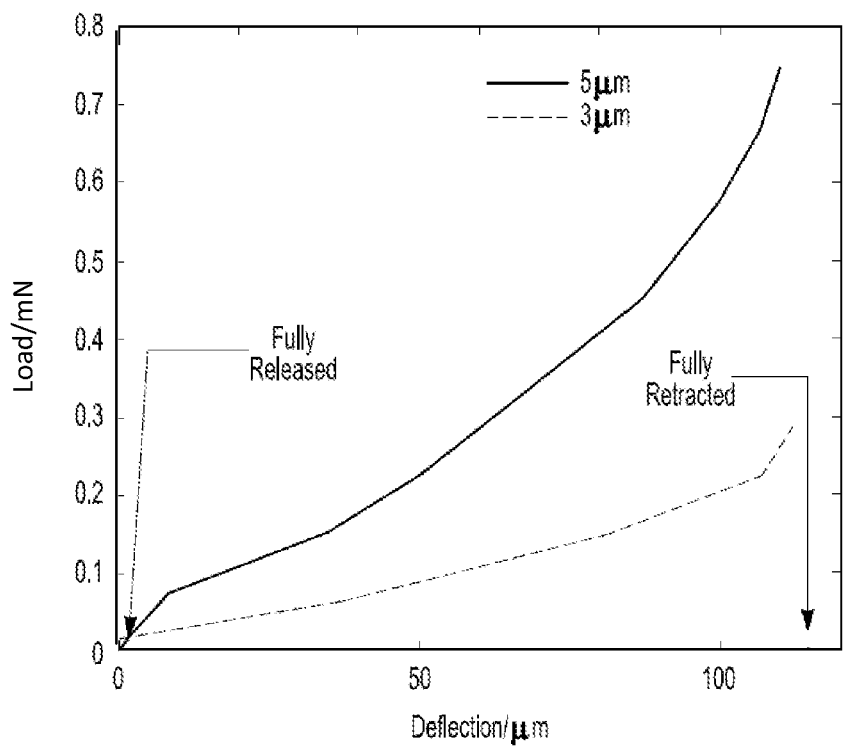
FIG. 13 is a force-deflection graph showing an example of force deflection relationships for two examples of spring actuators disclosed herein.

The springs 270 provide sufficient force to deploy the sites through biological tissue while remaining flexible enough to be retracted by capillary action forces or dip coating, and to be fixed by a dissolvable glue. Sufficient space should be provided such that interconnects can be routed on top of the springs, one per spring. To minimize the overall stiffness while allowing a reasonable interconnect density, two springs were stacked inside each other. The springs were made of silicon with a typical fracture stress of 7 GPa. The maximum stress in the springs was kept below 1 GPa. The shape of the springs 270 included two arcs facing in opposite directions. Rather than bend across a single joint, the springs 270 flex progressively to contact the surface of the shank 220 and the comb 244 when deflecting. The minimum radius of curvature for a given stress and displacement of the springs 270 is determined so that their length is minimized. The maximum stress found in a straight beam that is curled to an arc is inversely proportional to the radius of curvature and proportional to its thickness and Young's modulus. This relation may be used to approximate the stress in an arc that is forced into a straight form. This approach was closely verified in FEM simulations. Load deflection curves for the experimental springs are depicted in FIG. 13. The radius of curvature selected for the experimental examples was 420 μm yielding 120 μm displacement when the springs were 320 μm long. Both 3 μm and 5 μm wide springs were fabricated for experimentation. 3 μm wide springs were more flexible and easier to work with, while 5 μm wide springs allowed easy integration of interconnects. Designs with 3 μm wide springs were fabricated using deep reactive-ion etching (DRIE) on a Silicon on insulator (SOI) wafer with 15 μm thick structural layer and released in buffered hydrofluoric acid (BHF). The shanks 220 with 5 μm wide springs were fabricated using DRIE on a boron-doped wafer with a 15 μm deep etch stop and released in EDP (ethylenediamine-pyrocatechol-water). It is to be understood that other fabrication techniques are also possible and are contemplated as being within the purview of the present disclosure.

Figure 6:
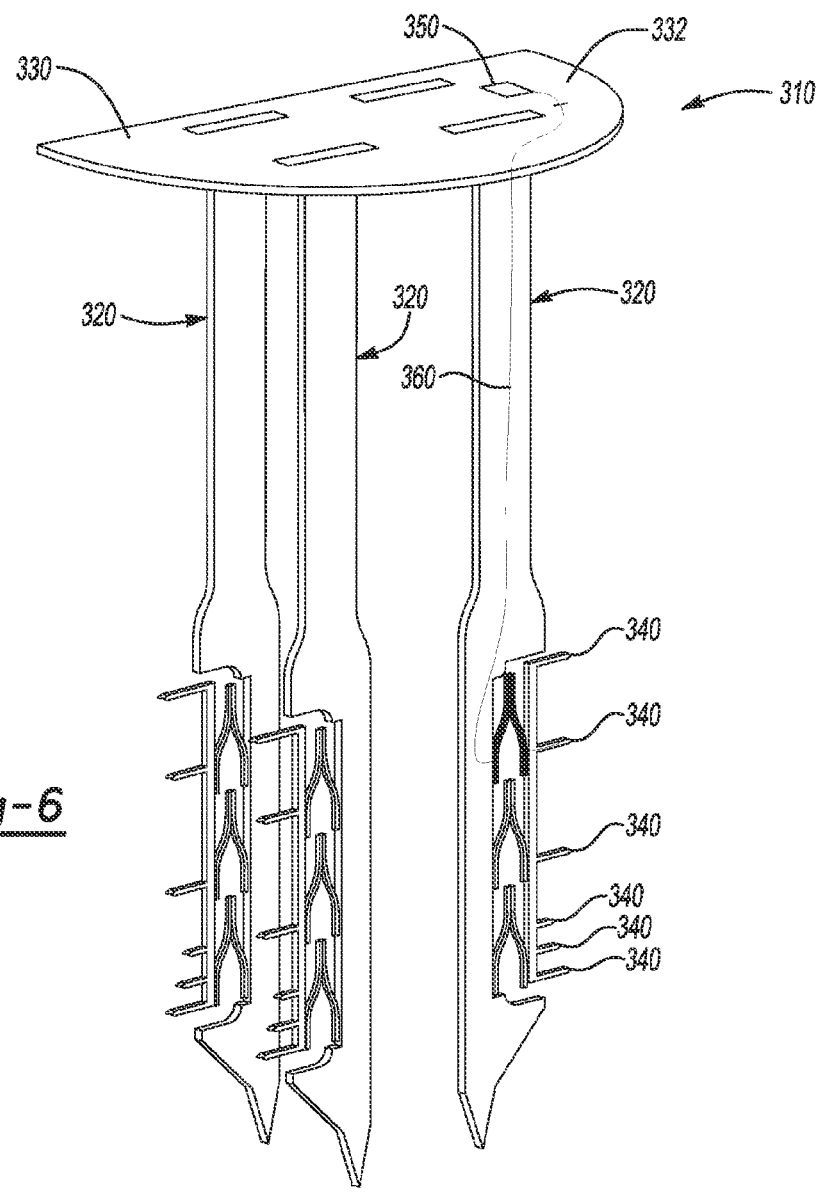
FIG. 6 is a semi-schematic view of the plurality of shanks shown in FIG. 5A, disposed in an array.

Referring now to FIG. 6, an example of the probe 310 disclosed herein includes a plurality of shanks arranged in an array insertable into the biological tissue as a single piece. As shown in FIG. 6, a plurality of shanks 320 similar to the shank 220 depicted in FIGS. 5A-5C has been disposed on a common platform 332. The platform 332 may function as the backend 330, or the platform 332 may be connected to a separate backend (not shown). FIG. 6 depicts an example of a connector 350 which is shown corresponding to a site 340. The site 340 is connected to the respective connector 350 by an insulated interconnect 360. A portion of the insulated interconnect 360 includes the wishbone-shaped spring colored dark in FIG. 6 to indicate that the wishbone-shaped spring is part of the insulated interconnect 360. The insulated interconnect 360 connects the connector 350 to the respective site 340. It is to be understood that a similar connector 350, and insulated interconnect 360 may correspond to each of the plurality of sites 340, but only one connector 350 and one insulated interconnect 360 are shown to improve readability of FIG. 6.

Figure 7A:
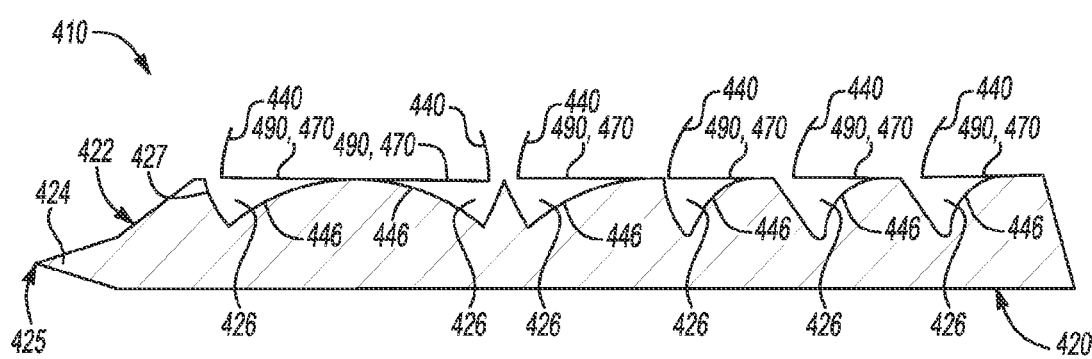
FIG. 7A is a semi-schematic view of a shank portion of an example of the probe disclosed herein with each site separately actuated by a respective separate cantilever spring.

FIG. 7A is a semi-schematic view of a portion of a shank 420 of an example of the probe 410 disclosed herein with each site 440 separately actuated by a respective separate cantilever spring 490. FIG. 7A depicts an example of the probe 410 disclosed herein with the sites 440 deployed away from the needle-shaped or blade-shaped shank 420. The shank 420 includes a sharp point 424 at the tip 425 of the leading edge 422 of the shank 420. The leading edge 422 may be wedge-shaped, having a trailing end 427 opposite the tip 425. The trailing end 427 may be larger than the point 424 in the dimension substantially perpendicular to the shank and substantially in the plane of the shank 420. The leading edge 422 is configured to cut a path into the biological tissue and move the biological tissue aside during insertion of the probe 410 into the biological tissue. Recessed areas 426 are defined along the shank 420 on one side of the shank 420. The recessed areas 426 are defined by a path swept by the each cantilever spring 490 as the cantilever spring 490 is retracted. It is to be understood that the cantilever springs 490 are elastic and may each conform to a curved surface in their respective retracted state. The recessed areas 426 define a protected area in which the sites 440 are less subject to damage during implantation of the probe 410 in biological tissue than areas outside of the protected area. As such, the recessed area 426 is shaped to selectively prevent direct exposure of the sites 440 to undisturbed areas of the biological tissue surrounding the shank 420 during and after implantation of the probe 410 in the biological tissue. It is to be understood that after the sites 440 have deployed into the biological tissue, the sites 440 tend to float with the biological tissue while remaining loosely connected to the probe 410.

Figure 7B:
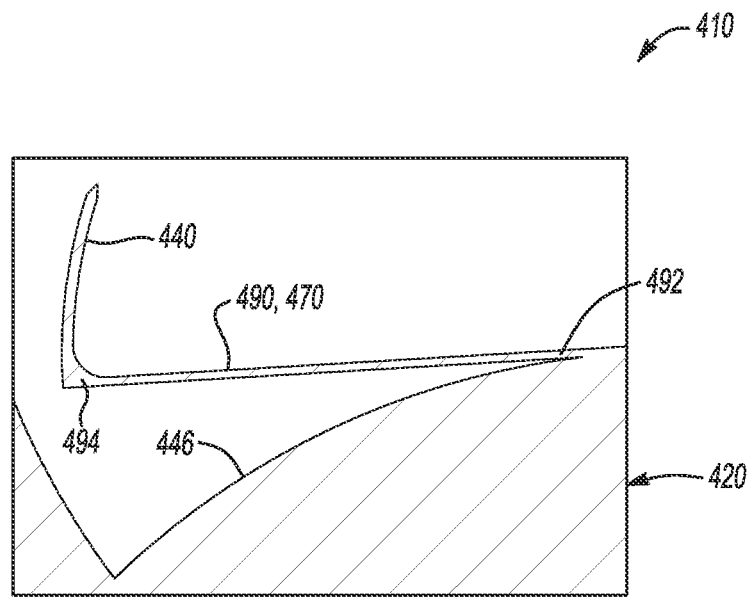
FIG. 7B is an enlarged view of an example of a cantilever spring and a site shown in the deployed position.
Figure 7C:
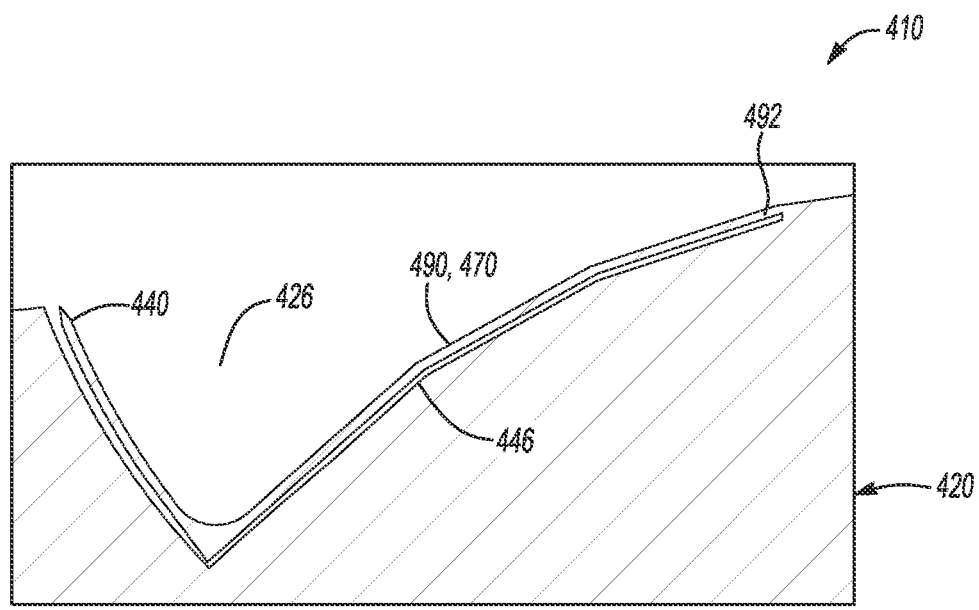
FIG. 7C is an enlarged view of the cantilever spring depicted in FIG. 7B shown in the retracted position with the site in the protected position.

FIG. 7B is an enlarged view of a cantilever spring 490 and a site 440 shown in the deployed position. Each cantilever spring 490 is a spring actuator 470. In the example depicted in FIGS. 7A-7C, each cantilever spring 490 may be a substantially straight beam (when in a free state) having a first end 492 rigidly disposed on the shank 420, and a free end 494 distal to the first end 492. A site 440 may be disposed on the cantilever spring 490. In the example, the sites are curved, needle-like structures that extend from the free end 494 of the spring 490. The curve of the needle-like site 440 corresponds to the curve traced by free end of the cantilever spring as the cantilever spring 490 is retracted. The position of the spring 490 and site 420 when the cantilever spring 490 is in the free state defines the deployed state for this particular example. It is to be understood that the cantilever springs 490 may be individually triggered. As such, the one site 440 may be in the deployed state while another site 440 may be in the retracted state. In the example shown in FIGS. 7A-7C, the shank includes a plurality of cantilever springs 490. Each cantilever spring 490 has a corresponding bed 446 defined in the shank 420. The surface of the bed 446 is gradually spaced away from the cantilever spring 490 in the free state, with the distance between the bed 446 and the surface increasing with the distance from the first end 492. When the cantilever spring 490 is in the retracted state (the spring contacts the bed 446 substantially along its entire length) the site is completely within the protected area. FIG. 7C is an enlarged view of the cantilever spring 490 depicted in FIG. 7B, shown in the retracted position with the site 440 in the protected position.

FIG. 8 is a semi-schematic view of an example of the probe 510 disclosed herein with an actuator that retracts from implantation forces. The probe 510 is depicted with the spring actuators 569, 571 in their free states and consequently, the sites 540, 540' are shown fully deployed. The shank 520 includes a sharp point 524 at the tip 525 of the leading edge 522 of the shank 520. As depicted in FIG. 8, in the free state, the leading edge 522 may be wedge-shaped, having a trailing end 527 opposite the tip 525. The trailing end 527 may be larger than the point 524 in the dimension substantially perpendicular to the shank 520 and substantially in the plane of the shank 520. The leading edge 522 is configured to cut a path into the biological tissue and move the biological tissue aside during insertion of the probe 510 into the biological tissue. The leading edge 522 may be disposed on a leading spring actuator 571. A first comb 544 includes a first spine 542 and a plurality of needle-like sites 540 projecting substantially parallel to each other orthogonal to the spine 542. A second comb 544' includes a second spine 542' and a plurality of needle-like sites 540' projecting substantially parallel to each other orthogonal to the spine 542'. The spines 542, 542' of the first comb 544 and the second comb 544' include a series of slots 548 spaced at intervals that correspond to a spacing of the needle-like sites 540, 540'. As shown in FIG. 8, the needle like sites 540 are disposed through the slots 548 in the second spine 542', and the needle like sites 540' are disposed through the slots 548 in the first spine 542. The leading spring actuator 571 may be elastically attached to the first spine 542 and the second spine 542'. A trailing spring actuator 569 may be attached to first spine 542 and the second spine 542' at an end of the spines 542, 542' distal to the leading spring actuator 571. Together, the trailing spring actuator 569, the leading spring actuator 571, the first spine 542, and the second spine 542' form a hexagon in the free state. When the shank 542 is thrust into biological tissue, the thrusting force causes the leading spring actuator to elastically distort from the free state, causing the spines 542, 542' to spread apart until, at a state where the spring actuators are nearly straightened, the needle-like sites 540, 540' are retracted to the maximum extent. When the probe 510 is in the target location in the biological tissue, the thrusting force is removed. In the absence of the thrusting force, the leading spring actuator 571 and the trailing spring actuator 569 relax and elastically return to their respective free states. As the spring actuators 569, 571 return to their free states, the spines 542, 542' will no longer hold the biological tissue away from the needle-like sites 540, 540', and the biological tissue will move over the needle-like sites 540, 540', being penetrated by the sites 540, 540' as the biological tissue settles into place. It is to be understood that the spring actuators 569, 571 may be bi-stable springs. Bi-stable springs have two free states. In the example depicted in FIG. 8, the probe 510 may be placed in a "cocked" state that holds the sites 540, 540' in a refracted position. By activating a trigger, chemically, thermally, or mechanically, the bi-stable springs may be switched to a deployed state, thereby deploying the sites 540, 540'.

FIGS. 9A and 9B depict a shank having a plurality of needle-like sites 640 disposed at an end of a shank 620. A protective cover 652 is disposed over the shank 620. The protective cover 652 has a plurality of grooves corresponding to the needle-like sites 640. The protective cover 652 includes a sharp point 624 at the tip 625 of the leading edge 622 of the protective cover 652. As depicted in FIGS. 9A and 9B, the leading edge 622 may be wedge-shaped, having a trailing end 627 opposite the tip 625. The trailing end 627 may be larger than the point 624 in the dimension substantially perpendicular to a longitudinal axis of the protective cover and substantially in the plane of the protective cover. The leading edge 622 is configured to cut a path into the biological tissue and move the biological tissue aside during insertion of the probe 610 into the biological tissue. When the probe 610 is in the target location in the biological tissue, the needle-like sites 640 may be selectively deployed. To deploy the needle-like sites 640, the shank 620 is translated toward the tip 625 such that the needle-like sites 640 are thrust through the slots 654 into the biological tissue.

FIG. 10 is a semi-schematic view of an example of the probe 710 disclosed herein with a hot-cold actuator. FIG. 10 depicts the sites 740 in the protected position. Thermal expansion or contraction causes the actuator 770 to warp, thereby deploying the comb 744 away from the protected area behind the leading edge 722 of the shank 720. The tip is indicated at reference numeral 725.

FIG. 11 is a semi-schematic view of an example of the probe 810 disclosed herein with a slide bar 864 locking the actuators 870 in the retracted position. The probe 810 is a variation on the probes depicted in FIGS. 2A-7C wherein rather than having a dissolvable glue retain the actuators in the retracted position, the slide bar 864 locks the actuators 870 in the retracted position. When the slide bar 864 is removed, the actuators 870 deploy and move the sites 840 to the deployed positions. The leading edge is indicated at reference numeral 822. The tip is indicated at reference numeral 825.

Figure 12:
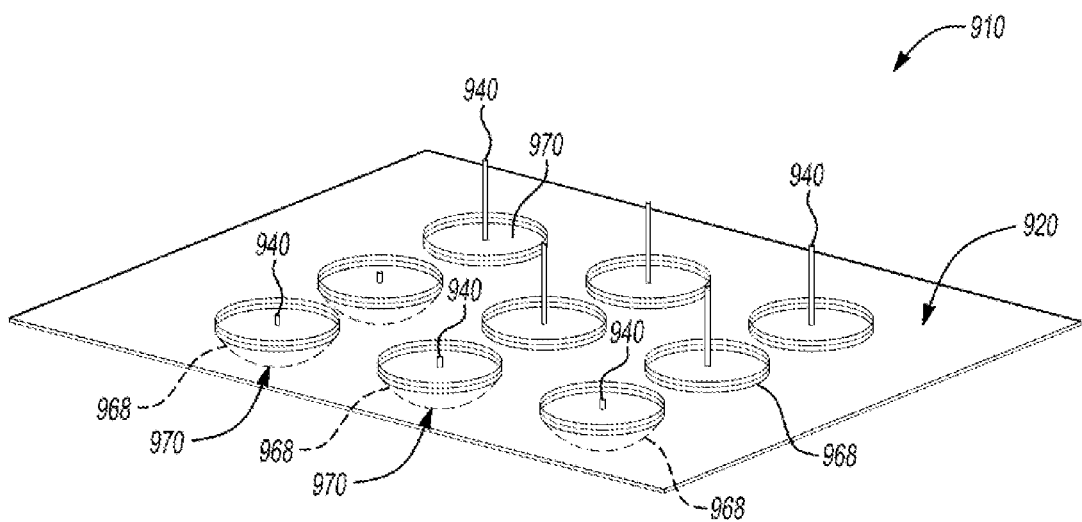
FIG. 12 is a semi-schematic view of an example of the probe disclosed herein with membrane actuators.

FIG. 12 is a semi-schematic view of an example of the probe 910 disclosed herein with membrane actuators 970. As depicted in FIG. 12, the shank 920 is a flat rectangle, and may include an array of membrane actuators 970 that are actuated by applying or reducing the pressure in balloon-like membranes 968. In the example depicted in FIG. 12, inflating the actuators 970 retracts the needle-like sites 940 into a protected area. When the pressure in the actuators 970 is removed, the actuators 970 elastically return to their free states, thereby deploying the needle-like sites 940 into the biological tissue.

FIG. 13 is a force-deflection graph showing force deflection relationships calculated in a simulation for two examples of spring actuators disclosed herein. The graph depicts spring actuators that are fully retracted when deflection is about 120 µm. The graph depicts spring actuators that are fully deployed when the deflection is 0 µm.

Interconnects are included in each example of the probe disclosed herein. The interconnects may be any of electrical conductors, semiconductors, optical waveguides, fluid conduits, and combinations thereof. The interconnects keep the sites connected to the connectors on the backend regardless of whether the probe is in the retracted state or the deployed state. As such, the interconnects should have sufficient flexibility to avoid fracturing or disrupting the transmission of signals or fluids as the probe changes states. The interconnects should also have sufficient robustness to the forces and displacements encountered during implantation and chronic use.

The interconnects may be incorporated into the spring structure. For example, if a spring is made from a conductive material, it can effectively be used as a wire to transmit signals. Spiral interconnects may be fabricated using MEMS fabrication technologies. These spiral interconnects may be used to flexibly connect the deployable sites to the shank so that signals or fluids may be transmitted. Flexible structures other than spirals may also be used; for example, zig-zag shapes, pantograph-like linkages, nets, diaphragms and fan-folded sheets may be used as interconnects. Tubes may be fabricated by etching out a trough, then depositing a cover over the trough. The trough may have undercuts.

In an example, surface tension disrupters may be included on a surface of an interconnect to prevent the interconnect from locking the sites in the retracted state. For example, symmetry-disrupting bumps or asperities may be fabricated into a surface to prevent surface tension from adversely affecting the deployment of the sites.

It is to be understood that the terms "connect/connected/connection" and/or the like are broadly defined herein to encompass a variety of divergent connected arrangements and assembly techniques. These arrangements and techniques include, but are not limited to (1) the direct communication between one component and another component with no intervening components therebetween; and (2) the communication of one component and another component with one or more components therebetween, provided that the one component being "connected to" the other component is somehow in operative communication with the other component (notwithstanding the presence of one or more additional components therebetween).

In describing and claiming the examples disclosed herein, the singular forms "a", "an", and "the" include plural referents unless the context clearly dictates otherwise.

It is to be understood that the ranges provided herein include the stated range and any value or sub-range within the stated range. For example, a range from 50 µm to about 100 µm should be interpreted to include not only the explicitly recited limits of 50 µm to about 100 µm, but also to include individual values, such as 50 µm, 75 µm, 95 µm, etc., and sub-ranges, such as from about 50 µm to about 80 µm, etc. Furthermore, when "about" is utilized to describe a value, this is meant to encompass minor variations (up to +/−10%) from the stated value.

While several examples have been described in detail, it will be apparent to those skilled in the art that the disclosed examples may be modified. Therefore, the foregoing description is to be considered non-limiting.

What is claimed is:

1. A probe for interfacing with biological tissue, comprising:
   a shank having a leading edge defined on the shank, the leading edge to cut a path into the biological tissue and move the biological tissue aside during insertion of the probe into the biological tissue;
   at least one site to monitor by receiving a signal from or to stimulate the biological tissue, the at least one site deployable from the shank;
   at least one insulated interconnect connected to the at least one site, to guide electrical signals between the at least one site and the shank; and
   at least one actuator to displace the at least one site away from a respective protected position defined by a recessed area defined along the shank and defined on the shank to a respective deployed position in the biological tissue to be monitored or stimulated by the at least one site.

2. The probe as defined in claim 1 wherein the deployed position in the biological tissue to be monitored is beyond scar tissue formed as an immune response to the probe, and wherein the deployed position is spaced at least about 50 µm from the protected position.

3. The probe as defined in claim 1 wherein the at least one site in the deployed position remains loosely connected to the probe so that the at least one site is floatable with the biological tissue.

4. The probe as defined in claim 1 wherein the deployed position is spaced at least about 1 µm from the protected position.

5. The probe as defined in claim 1 wherein the actuator is a mechanical spring.

6. The probe as defined in claim 5 wherein capillary action forces cause the actuator to retract the at least one site into the protected position upon exposure of the actuator to a wetting fluid.

7. The probe as defined in claim 5, further comprising a shrinking gel that causes the actuator to retract the at least one site into the protected position upon exposure of the actuator to a fluid including the gel and subsequent drying of the fluid.

8. The probe as defined in claim 5, further comprising a glue, wherein the actuator is releasably retained in the retracted position by the glue that is dissolvable in the biological tissue.

9. The probe as defined in claim 8 wherein the glue is chosen from sugar, agar gel, sugar saccharides, gelatin, or combinations thereof.

10. The probe as defined in claim 5 wherein the spring is bi-stable.

11. The probe as defined in claim 5 wherein the spring is retracted by forces on a tip during implantation and wherein the spring is automatically released when the implantation forces on the tip are removed.

12. The probe as defined in claim 5 wherein the spring is a balloon actuator retracted by pressure and actuated by stored elastic energy.

13. The probe as defined in claim 5 wherein the actuator is caused to retract the at least one site to the respective protected position by a retraction mechanism chosen from the group consisting of: a common micro manipulator stage; a forced convection fluid stream by direct impingement; and a forced convection fluid stream by fluid motion-generated pressure differential.

14. The probe as defined in claim 1 wherein the actuator is passively triggered by a change of environment during or after implantation.

15. The probe as defined in claim 1 wherein the actuator is activated by a chemical reaction that changes an adhesive layer or by a chemical reaction wherein the chemical reaction is initiated by a change of pH, humidity, temperature or magnetic field strength.

16. The probe as defined in claim 1 wherein the actuator is integrated into the probe.

17. The probe as defined in claim 1 wherein the at least one site includes an electrode, a chemical sensor, or combinations thereof.

18. The probe as defined in claim 17 wherein the at least one site further includes an opening of an optical waveguide, a port for fluid flow, a structure for drug release, or combinations thereof.

19. The probe as defined in claim 1 wherein the at least one shank is a plurality of shanks arranged in an array insertable in the biological tissue as a single piece.

20. The probe as defined in claim 1 wherein the deployed position in the biological tissue to be monitored or stimulated is spaced from about 50 μm to about 150 μm from the protected position.

* * * * *